US009676737B2

(12) United States Patent
Dethlefsen et al.

(10) Patent No.: US 9,676,737 B2
(45) Date of Patent: Jun. 13, 2017

(54) PROCESS FOR FUNCTIONALIZING BIOMASS USING MOLYBDENUM CATALYSTS

(71) Applicant: Danmarks Tekniske Universitet, Lyngby (DK)

(72) Inventors: Johannes Rytter Dethlefsen, Brønshøj (DK); Peter Fristrup, Virum (DK)

(73) Assignee: Danmarks Tekniska Universitet, Kgs. Lyngby (DK)

( * ) Notice: Subject to any disclaimer, the term of this patent is extended or adjusted under 35 U.S.C. 154(b) by 0 days.

(21) Appl. No.: 14/915,114

(22) PCT Filed: Aug. 29, 2014

(86) PCT No.: PCT/DK2014/050258
§ 371 (c)(1),
(2) Date: Feb. 26, 2016

(87) PCT Pub. No.: WO2015/028028
PCT Pub. Date: Mar. 5, 2015

(65) Prior Publication Data
US 2016/0200641 A1    Jul. 14, 2016

(30) Foreign Application Priority Data

Aug. 29, 2013    (EP) .................................... 13182179

(51) Int. Cl.
| | |
|---|---|
| *C07C 1/00* | (2006.01) |
| *C07C 27/04* | (2006.01) |
| *C07D 301/02* | (2006.01) |
| *C07C 45/00* | (2006.01) |
| *C07C 29/60* | (2006.01) |
| *C07C 1/22* | (2006.01) |
| *C07C 45/52* | (2006.01) |
| *C07D 303/04* | (2006.01) |

(52) U.S. Cl.
CPC .............. *C07D 301/02* (2013.01); *C07C 1/22* (2013.01); *C07C 29/60* (2013.01); *C07C 45/00* (2013.01); *C07C 45/52* (2013.01); *C07D 303/04* (2013.01); *C07C 2527/24* (2013.01); *C07C 2531/16* (2013.01); *C07C 2531/18* (2013.01); *C07C 2531/34* (2013.01)

(58) Field of Classification Search
CPC ........... C07C 1/22; C07C 45/00; C07C 29/60; C07C 45/52; C07C 33/03; C07C 49/04; C07C 11/107; C07C 11/02; C07C 11/10; C07D 301/02
USPC ....................................................... 549/518
See application file for complete search history.

(56) References Cited

U.S. PATENT DOCUMENTS

| | | |
|---|---|---|
| 5,616,817 A | 4/1997 | Schuster |
| 8,273,926 B2 | 9/2012 | Bergman |
| 2009/0054701 A1 | 2/2009 | Abhari |

FOREIGN PATENT DOCUMENTS

| | | |
|---|---|---|
| DE | 10 2008 031 828 A1 | 1/2010 |
| EP | 0 415 202 A2 | 3/1991 |
| WO | WO 2008/092115 A1 | 7/2008 |

OTHER PUBLICATIONS

Ahmad, Irshad et al., "Sulfite-Driven, Oxorhenium-Catalyzed Deoxydehydration of Glycols" Organometallics, pp. 2810-2818, vol. 30.
Arceo, Elena et al., "Rhenium-Catalyzed Didehydroxylation of Vicinal Diols to Alkenes Using a Simple Alcohol as a Reducing Agent" J. Am. Chem. Soc., 2010, pp. 11408-11409, vol. 132.
Boucher-Jacobs, Camille et al., "Catalytic Deoxydehydration of Glycols with Alcohol Reductants" ChemSusChem, 2013, pp. 597-599, vol. 6.
Cook, Gerald K. et al., "Towards Nonoxidative Routes to Oxygenated Organics: Stereospecific Deoxydehydration of Diols and Polyols to Alkenes and Allylic Alcohols Catalyzed by the Metal Oxo Complex $(C_5Me_5)ReO_3$" J. Am. Chem. Soc., 1996, pp. 9448-9449, vol. 118.
Dethlefsen, Johannes R. et al., "Molybdenum-Catalyzed Deoxydehydration of Vicinal Diols" ChemSusChem, 2014, pp. 425-428, vol. 7.
Hills, Lily et al., "Dioxomolybdenum(VI) Complexes with Acylpyrazolonate Ligands: Synthesis, Structures, and Catalytic Properties" Eur. J. Inorg. Chem., 2013, pp. 3352-3361.
Shiramizu, Mika et al., "Deoxygenation of Biomass-Derived Feedstocks: Oxorhenium-Catalyzed Deoxydehdration of Sugars and Sugar Alcohols" Angew. Chem. Int. Ed., 2012, pp. 8082-8086, vol. 51.
Suprun, Wladimir el al., "Catalytic activity of bifunctional transition metal oxide containing phosphated alumina catalysts in the dehydration of glycerol" Jounral of Molecular Catalysis A: Chemical, 2011, pp. 91-100, vol. 342-343.
Vkuturi, Saidi et al., "Rhenium-Catalyzed Deoxydehydration of Glycols by Sulfite"Inorg. Chem. 2010, pp. 4744-4746, vol. 49.
Yi, Jing et al., "Rhenium-Catalyzed Transfer Hydrogenation and Deoxygenation of Biomass-Derived Polyols to Small and Useful Organics"ChemSusChem, 2012, pp. 1401-1404, vol. 5.
Zieglar, Jeanette E. et al., "$H_2$—Driven Deoxygenation of Epoxides and Diols to Alkenes Catalyzed by Methyltrioxorhenium"Inorg. Chem., 2009, pp. 9998-10000, vol. 48.
International Search Report for PCT/DK2014/050258 dated Nov. 3, 2014.
Dethlefsen, Johannes R. et al., "Molybdenum-Catalyzed Conversion of Diols and Biomass-Derived Polyols to Alkenes Using Isopropyl Alcohol as Reductant and Solvent" ACS Catalysis, 2015, pp. 3638-3647, vol. 5.

*Primary Examiner* — T. Victor Oh
(74) *Attorney, Agent, or Firm* — Knobbe, Martens, Olson & Bear, LLP

(57) ABSTRACT

The present invention concerns a process for converting biomass into useful organic building blocks for the chemical industry. The process involves the use of molybdenum catalysts of the formula $A^{a+}a(Mo_vX_xR^1_yR^2_zR^3e)^{a*3-}$, which may be readily prepared from industrial molybdenum compounds.

22 Claims, No Drawings

PROCESS FOR FUNCTIONALIZING BIOMASS USING MOLYBDENUM CATALYSTS

CROSS REFERENCE TO RELATED APPLICATIONS

This application is a U.S. National Phase Application of PCT International Application Number PCT/DK2014/050258, filed on Aug. 29, 2014, designating the United States of America and published in the English language, which is an International Application of and claims the benefit of priority to European Patent Application No. 13182179.5, filed on Aug. 29, 2013. The disclosures of the above-referenced applications are hereby expressly incorporated by reference in their entireties.

FIELD OF THE INVENTION

The present invention concerns a process for converting biomass into useful building blocks for the chemical industry. The process involves the use of molybdenum-based catalysts, which may be readily prepared from industrial molybdenum compounds.

BACKGROUND OF THE INVENTION

The chemistry building blocks used in industrial polymers, fine chemicals etc. are typically prepared from fossil fuels. However, the use of fossil fuel-based building blocks is not sustainable, and it is therefore necessary to find alternative ways of preparing these building blocks.

Biomass and waste products from processes including biomass contain more oxygen than the products obtained from fossil fuels, and they are therefore not immediately useful in preparing organic chemistry building blocks. One example of a waste product obtained from processing biomass is glycerol, which is a byproduct from biodiesel production. According to Ullmann's Encyclopedia of Industrial Chemicals, the production of glycerol will be six times higher than the demand by 2020. Glycerol is not useful as such as a building block, but if it is reduced to allyl alcohol, it could serve as a building block.

U.S. Pat. No. 8,273,926 concerns a method for converting a polyol to the corresponding olefin by heating with formic acid. One of the polyols tested in this patent is glycerol. The disadvantages of the method include the need of carrying out three formic acid treatment/distillation/cooling to room temperature cycles, the use of an inert atmosphere, and the separation of allyl alcohol from formic acid.

Yi et al., *ChemSusChem*, 2012, vol. 5, 1401-1404, describe rhenium-catalyzed deoxygenation of glycerol, erythritol, and threitol. The authors also tested $(NH_4)_2MoO_4$ at 165° C. but were unable to isolate any products. The disadvantage of using rhenium-based catalysts is the high price of the non-abundant metal.

Hills et al., *Eur. J. Inorg. Chem.*, 2013, 3352-3361, tested several molybdenum catalysts bearing rather complex acylpyrazolonate ligands in deoxygenation reactions of 1-phenylethane-1,2-diol and 1,2-cyclooctanediol. They also tested two catalysts without the complex ligand ($MoO_3$ and $(NH_4)_6Mo_7O_{24}\cdot 4H_2O$) but were unable to isolate any styrene using the reactive styrene oxide as substrate. Styrene oxide is very different from typical biomass-derived polyols as it is activated in the benzylic position.

DE 102008031828, U.S. Pat. No. 5,616,817, US 2009/054701, EP 0415202, and Suprun et al. (Journal of Molecular Catalysis A, vol. 342, 91-100) all disclose the reduction of polyols using a catalyst that involves a minor amount of molybdenum. However, common to all these documents is that none of them disclose all the reactants being dissolved in the common reaction medium, some of them even concerning gas phase reaction. Furthermore, U.S. Pat. No. 5,616,817 and EP 0415202 describe the reduction of the catalyst with hydrogen prior to reaction, meaning that the catalyst in question in fact contains metallic molybdenum.

Hence, there exists a need for an improved process for reducing biomass and biomass-derived compounds in an efficient and cost-effective manner. Preferably, the process should involve a catalyst that is either already commercially available or is readily prepared from commercially available compounds.

SUMMARY OF THE INVENTION

Accordingly, the present invention concerns in one aspect a process for the reduction of a polyol comprising the reaction of the polyol with a substrate in the presence of a molybdenum catalyst at a temperature of at least 175° C., wherein said molybdenum catalyst has the formula:

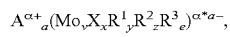

$$A^{\alpha+}{}_a(Mo_vX_xR^1{}_yR^2{}_zR^3{}_e)^{\alpha*a-},$$

and wherein
$A^{\alpha+}$ is a mono-, di-, or trivalent counterion;
X is CO, O, OH, S, or Se;
$R^1$ is selected from the group consisting of H, F, Cl, Br, I, CN, $N_3$, NCS, dithiocarbamates, $CH_3$, $BF_4$, $PF_6$, $SbF_6$, and $AsF_6$;
$R^2$ is a mono-, bi- or tridentate ligand;
$R^3$ is a ligand coordinating to the central molybdenum atom through its π-system selected from the group consisting of an alkene, a diene, a cyclopentadienyl, methylcyclopentadienyl, or pentamethylcyclopentadienyl radical, benzene, naphthalene, anthracene, or other aromatics;
a is 0, 1, 2, 3, 4, 5, or 6;
v is 1, 2, 3, 4, 5, 6, or 7;
x is in the range 2v to 6v;
y is 0, 1, 2, 3, 4, 5, 6, 7, or 8;
z is 0, 1, 2, or 3; and
e is 0, 1, 2, or 3.

The process according to the invention uses a slightly higher temperature than the processes disclosed by Yi et al. and Hills et al., who obtained no reduction product. It is therefore surprising that the present invention obtains high yields of reduction products using commercially available molybdenum catalysts.

DETAILED DISCLOSURE OF THE INVENTION

Definitions

In the context of the present invention, the term "glycerol" is intended to mean the chemical compound $HOCH_2CHOHCH_2OH$, which is also commonly referred to as 1,2,3-trihydroxypropane or glycerin.

In the context of the present invention, the term "diol" is intended to mean an organic chemical compound containing two hydroxyl groups.

In the context of the present invention, the term "triol" is intended to mean an organic chemical compound containing three hydroxyl groups.

In the context of the present invention, the term "polyol" refers to a polyhydric alcohol, or polyalcohol, that is, an alcohol containing a plurality of hydroxyl groups, wherein at least two of the hydroxyl groups are located on adjacent carbon atoms.

In the context of the present invention, the term "sugar polyol", also known as alditol, is intended to mean a hydrogenated form of carbohydrate whose carbonyl group (aldehyde or ketone) has been reduced to a primary or secondary hydroxyl group.

In the context of the present invention, the term "donor atom" is intended to mean the atom directly attached to the molybdenum atom. The term "monodentate ligand" is intended to mean a ligand having one donor atom. The term "bidentate ligand" is intended to mean a ligand having two donor atoms. The term "tridentate ligand" is intended to mean a ligand having three donor atoms.

In the context of the present invention, a "reductant" is intended to mean a reactant of the process of the invention that serves to reduce another reactant, such as the polyol. In the context of the present invention, an "oxidant" is intended to mean a reactant of the process of the invention that serves to oxidize another reactant, such as the polyol.

In one aspect of the present invention, it concerns a process for the reduction of a polyol comprising the reaction of the polyol with a substrate in the presence of a molybdenum catalyst at a temperature of at least 175° C., wherein said molybdenum catalyst has the formula:

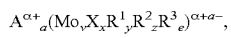

and wherein $A^{\alpha+}$ is a mono-, di-, or trivalent counterion;
X is CO, O, OH, S, or Se;
$R^1$ is selected from the group consisting of H, F, Cl, Br, I, CN, $N_3$, NCS, dithiocarbamates, $CH_3$, $BF_4$, $PF_6$, $SbF_6$, and $AsF_6$;
$R^2$ is a mono-, bi- or tridentate ligand;
$R^3$ is a ligand coordinating to the central molybdenum atom through its π-system selected from the group consisting of an alkene, a diene, a cyclopentadienyl, methylcyclopentadienyl, or pentamethylcyclopentadienyl radical, benzene, naphthalene, anthracene, or other aromatics;
a is 0, 1, 2, 3, 4, 5, or 6;
v is 1, 2, 3, 4, 5, 6, or 7;
x is in the range 2v to 6v;
y is 0, 1, 2, 3, 4, 5, 6, 7, or 8;
z is 0, 1, 2, or 3; and
e is 0, 1, 2, or 3.

Temperature

As mentioned above, the temperature of the process of the present invention has been found to be an important parameter in obtaining a yield of reaction products. It has been found that the reaction temperature is advantageously at least 175° C. There is in principle no upper limit on the reaction temperature, except for the boiling points of the various reagents and solvents. However, it would be less than economical to run the reaction at a higher temperature than the temperature necessary to optimize the yield.

Accordingly, in one embodiment, the temperature is in the range 175 to 250° C. In another embodiment, the temperature is in the range 180 to 220° C. In yet another embodiment, the temperature is in the range 190 to 210° C. In a further embodiment, the temperature is in the range 195 to 205° C.

Polyol

The process of the present invention achieves the reduction of biomass material or biomass-derived byproducts. Common to these biomass products is that they are polyols in the meaning used in the present context. Biomass-derived material may contain larger molecules, such as macromolecules, wherein only parts of the molecule contain a plurality of hydroxyl groups. The present invention is also intended to encompass these molecules in the process.

The polyol can be cyclic or acyclic. In one embodiment of the invention, the polyol is a diol or triol. In a further embodiment, the polyol is selected from the group consisting of 1,2-hexanediol, 1,2-tetradecanediol, and glycerol. In still a further embodiment, the polyol is a diol. In yet a further embodiment, the polyol is a triol.

In another embodiment of the invention, the diol is 1,2-propanediol, 1,2-butanediol, 1,2-pentanediol, 1,2-hexanediol, 1,2-octanediol, 1,2-decanediol, 1,2-dodecanediol, 1,2-tetradecanediol, 1,2-cyclooctanediol, 1,2-cyclohexanediol, 1,2-cyclopentanediol, 1,4-anhydroerythritol, or a mixture thereof.

In yet another embodiment of the invention, the triol is glycerol, 1,2,6-trihydroxyhexane, 1,2,3-butanetriol, 1,2,3-hexanetriol, 1,2,3-cyclohexanetriol, or a mixture thereof.

An important byproduct in biodiesel production is glycerol. Hence, in still another embodiment, the triol is glycerol.

In a further embodiment of the invention, the polyol is a sugar polyol, monoanhydro sugar polyol, sugar, or a mixture thereof. In yet a further embodiment of the invention, the polyol is xylitol, sorbitol, arabinitol, ribitol, mannitol, galactitol, iditol, erythritol, threitol, isomalt, lactitol, quinic acid, shikimic acid, or a mixture thereof. In still a further embodiment of the invention, the polyol is glucose, fructose, sucrose, lactose, maltose, or a mixture thereof.

Substrate

A reduction reaction requires a reductant, which in turn is oxidized in the reaction. Similarly, an oxidation reaction requires an oxidant, which in turn is reduced in the reaction. A number of different substrates will be reduced or oxidized in the presence of the polyol and molybdenum catalysts according to the present invention. The versatility of the molybdenum catalyst in the process of the present invention is illustrated by the fact that the polyol itself may serve both as oxidant and reductant, i.e. for each two molecules of polyol one is reduced and the other oxidized. Hence, in one embodiment of the present invention, the substrate is the polyol itself. Evidently, the maximum theoretical yield of one product in this reaction is 50%.

Furthermore, since the polyol is capable of reducing/oxidizing itself, it is also clear that other polyols than the polyol being reduced/oxidized may serve as the substrate. Hence, in one embodiment, the substrate is a polyol different from the polyol being reduced or oxidized in the process of the invention.

Another example of a substrate, which does not necessarily meet the definition of polyol in the context of the present invention, is a diol. The diol substrate may or may not have hydroxyl groups on adjacent carbon atoms. Accordingly, in one embodiment of the present invention, the substrate is a diol different from the polyol, such as 1,5-pentanediol or 1,6-hexanediol, in particular 1,5-pentanediol.

A reductant typically applied in organic chemistry is gaseous hydrogen. It has been found that this reductant also works as a substrate in the process of the present invention. Evidently, when using hydrogen gas as the substrate, the polyol is reduced in the process according to the present invention. Thus, in another embodiment, the substrate is a reductant. In yet another embodiment, the substrate is gaseous hydrogen. An advantage of using gaseous hydrogen as the substrate is that the resulting product is water.

Molybdenum Catalyst

The molybdenum catalyst employed in the process of the present invention has the formula:

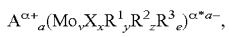

$$A^{\alpha+}{}_a(Mo_vX_xR^1{}_yR^2{}_zR^3{}_e)^{\alpha*a-},$$

wherein
A$^{\alpha+}$ is a mono-, di-, or trivalent counterion;
X is CO, O, OH, S, or Se;
R$^1$ is selected from the group consisting of H, F, Cl, Br, I, CN, N$_3$, NCS, dithiocarbamates, CH$_3$, BF$_4$, PF$_6$, SbF$_6$, and AsF$_6$;
R$^2$ is a mono-, bi- or tridentate ligand;
R$^3$ is a ligand coordinating to the central molybdenum atom through its rt-system selected from the group consisting of an alkene, a diene, a cyclopentadienyl, methylcyclopentadienyl, or pentamethylcyclopentadienyl radical, benzene, naphthalene, anthracene, or other aromatics;
a is 0, 1, 2, 3, 4, 5, or 6;
v is 1, 2, 3, 4, 5, 6, or 7;
x is in the range 2v to 6v;
y is 0, 1, 2, 3, 4, 5, 6, 7, or 8;
z is 0, 1, 2, or 3; and
e is 0, 1, 2, or 3.

The element molybdenum can exist in a number of oxidation states from −2 to +6. The molybdenum used in the molybdenum catalyst according to the present invention may be in any one of these oxidation states. However, some oxidation states are more frequently encountered than others. Thus, in one embodiment Mo is Mo(O), Mo(IV), or Mo(VI), in particular Mo(VI).

The molybdenum catalyst may contain a mono-, di-, or trivalent counterion, A$^{\alpha+}$. This counterion may be selected from the group consisting of simple metal cations (Li$^+$, Na$^+$, K$^+$, Rb$^+$, Cs$^+$, Be$^{2+}$, Mg$^{2+}$, Ca$^{2+}$, Sr$^{2+}$, Ba$^{2+}$, Al$^{3+}$, Ga$^{3+}$, In$^{3+}$, Tl$^+$, Sn$^{2+}$, Pb$^{2+}$, Bi$^{3+}$, Sc$^{3+}$, Y$^{3+}$, Ti$^{2+}$, Ti$^{3+}$, V$^{2+}$, V$^{3+}$, Cr$^{2+}$, Cr$^{3+}$, Mn$^{2+}$, Mn$^{3+}$, Fe$^{2+}$, Fe$^{3+}$, Ru$^{2+}$, Ru$^{3+}$, Co$^{2+}$, Co$^{3+}$, Rh$^{3+}$, Ir$^{3+}$, Ni$^{2+}$, pd$^{2+}$, pt$^{2+}$, Cu$^+$, Cu$^{2+}$, Ag$^+$, Au$^+$, Au$^{3+}$, Zn$^{2+}$, Cd$^{2+}$, Hg$^{2+}$, La$^{3+}$, and other lanthanides), H$^+$, NH$_{4+}$, and alkyl-substituted ammonium ions, and pyridinium. In one embodiment, A$^{\alpha+}$ is Na$^+$ or NH$_{4+}$.

The X component may be any one of CO, O, OH, S, Se, or mixtures thereof. In one embodiment, X is CO or O. In another embodiment, X is O. In yet another embodiment, X is CO.

R$^1$ may be selected from any one of H, F, Cl, Br, I, CN, N$_3$, NCS, dithiocarbamates, CH$_3$, BF$_4$, PF$_6$, SbF$_6$, and AsF$_6$, and mixtures thereof. In one embodiment, R$^1$ is selected from the group consisting of CH$_3$, Br, Cl, and mixtures thereof. In a further embodiment, R$^1$ is CH$_3$. In yet a further embodiment, R$^1$ is Br. In still a further embodiment, R$^1$ is Cl.

The R$^2$ ligand may in principle have any electron-donating element as the donor atom. In one embodiment, R$^2$ has one or more donor atoms selected from the group consisting of N, P, and S. In another embodiment, R$^2$ has one or more nitrogen atoms as donor atoms. In yet another embodiment, R$^2$ is 2,2'-bipyridine, 1,10-phenanthroline, trispyrazolylborate, ethylenediamine, or Ph$_2$PN(R)PPh$_2$, wherein Ph is phenyl and wherein R is cyclohexyl, phenyl, or benzyl. In still another embodiment, R$^2$ is 2,2'-bipyridine.

The R$^2$ ligand may be mono-, bi-, or tridentate. In one embodiment, R$^2$ is a bidentate ligand.

The R$^3$ ligand may have a hapticity of 2, 3, 5 or 6. It coordinates to the central molybdenum atom through its π system. In one embodiment, R$^3$ is selected from the group consisting of η$^5$-cyclopentadienyl, η$^5$-methylcyclopentadienyl, η$^5$-pentamethylcyclopentadienyl, η$^6$-benzene, η$^6$-toluene, η$^6$-cymene, η$^6$-naphthalene, η$^6$-anthracene, η$^3$-propenyl.

The value of the various parameters, a, v, x, y, z, and e, may vary. In one embodiment, a is 0, 2, or 6. In another embodiment, v is 1 or 7, in particular 1. The parameter x is in the range 2v to 6v, that is, it may be any integer number in the range 2v to 6v. As an example, if v is 1, then x may be 2, 3, 4, 5, or 6. In one embodiment, x is 2, 4, 6, or 24.

R$^1$ may be present in the catalyst or it may not be present. Accordingly, y is 0, 1, 2, 3, 4, 5, 6, 7, or 8. In one embodiment, y is 0 or 2. The ligand R$^2$ may also be absent in the molybdenum catalyst. Accordingly, z is 0, 1, 2, or 3. In one embodiment, z is 0 or 1. R$^3$ may also be absent and is not present in the molybdenum catalyst at the same time as R$^2$. Accordingly, at least one of z and e is 0.

The individual embodiments for each of the parameters a, v, x, y, z, and e, may be combined according to the present invention. Hence, in one further embodiment, a is 0, 2, or 6, v is 1 or 7, x is 2, 4, 6, or 24, y is 0 or 2, z is 0 or 1, and e is 0.

Concrete examples of molybdenum catalysts effective in the process of the invention are Mo(CO)$_6$, Mo(CO)$_4$(bipy), MoO$_2$Cl$_2$(bipy), MoO$_2$Br$_2$(bipy), MoO$_2$(CH$_3$)$_2$(bipy), (NH$_4$)$_6$Mo$_7$O$_{24}$·4H$_2$O, and Na$_2$MoO$_4$, wherein bipy is 2,2'-bipyridine. Accordingly, in one embodiment, the molybdenum catalyst is selected from the group consisting of Mo(CO)$_6$, Mo(CO)$_4$(bipy), MoO$_2$Cl$_2$(bipy), MoO$_2$Br$_2$(bipy), MoO$_2$(CH$_3$)$_2$(bipy), (NH$_4$)$_6$Mo$_7$O$_{24}$·4H$_2$O, Na$_2$MoO$_4$, and mixtures thereof, wherein bipy is 2,2'-bipyridine. In a further embodiment, the molybdenum catalyst is selected from the group consisting of MoO$_2$Cl$_2$(bipy), MoO$_2$Br$_2$(bipy), MoO$_2$(CH$_3$)$_2$(bipy), (NH$_4$)$_6$Mo$_7$O$_{24}$·4H$_2$O, Na$_2$MoO$_4$, and mixtures thereof, wherein bipy is 2,2'-bipyridine. In yet a further embodiment, the molybdenum catalyst is (NH$_4$)$_6$Mo$_7$O$_{24}$·4H$_2$O.

The amount of molybdenum catalyst used in the process of the invention may vary within a wide range. The amount is balanced by the requirement that enough catalyst is present to catalyse the process on the one hand and the requirement that the process remains economical on the other hand. Accordingly, in one embodiment, the amount of molybdenum catalyst is in the range 0.1 to 20 mol %. In another embodiment, the amount of molybdenum catalyst is in the range 1 to mol %. In yet another embodiment, the amount of molybdenum catalyst is in the range 2 to 10 mol %. In still another embodiment, the amount of molybdenum catalyst is in the range 3 to 8 mol %. In a further embodiment, the amount of molybdenum catalyst is in the range 4 to 7 mol %, such as approximately 5 mol %.

Solvent

The polyol being reduced in the process according to the present invention may also act as a solvent. Hence, the process may be carried out with or without an additional solvent. Accordingly, in one embodiment the process is carried out without a solvent in addition to the polyol. The substrate may also act as a solvent. Thus, in another embodiment, the substrate is the only other solvent than the polyol. In still a further embodiment, the solvent is a solvent different from both the polyol and the substrate.

If an additional solvent is used, it should preferably be chosen so that the solubility of the polyol, the substrate, and the molybdenum catalyst is high enough to fully dissolve all of these components. Suitable solvents for the process of the present invention include water, super-critical water, super-critical CO$_2$, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, decane, undecane, dodecane, tridecane, tetradecane, pentadecane, hexadecane, diglyme, triglyme, tetraglyme, diethyleneglycol, triethyleneglycol, DMF, NMP, triacetin, or mixtures thereof.

The Product

Depending on the exact reaction conditions, the product of the process may vary. As an example, the reaction conditions and the substrate determine whether the substrate acts a reductant or an oxidant. In one embodiment, the polyol is being reduced. In another embodiment, the resulting product of the process according to the present invention having the highest molar percentage is the compound corresponding to the polyol wherein at least one α,β-dihydroxyl group has been converted into an α,β-carbon-carbon double bond or the compound corresponding to the polyol wherein at least one α,β-dihydroxyl group has been converted into an α,β-epoxy group. In yet another embodiment, the resulting product of the process according to the present invention having the highest molar percentage is the compound corresponding to the polyol wherein at least one α,β-dihydroxyl group has been converted into an α,β-carbon-carbon double bond.

An example of the latter is when the polyol has at least three adjacent hydroxyl groups and is converted into the corresponding allylic alcohol. Hence, in a further embodiment, the resulting product of the process according to the invention having the highest molar percentage is the allylic alcohol corresponding to a polyol having at least three adjacent hydroxyl groups. In yet a further embodiment the polyol is glycerol and it is converted into allyl alcohol.

Additional Embodiments

The inventors of the present invention have found that the yield does not depend significantly on whether it is carried out under an inert atmosphere or not. However, circumstances may dictate that an inert atmosphere is used. Thus, in one embodiment, the process is carried out under an inert atmosphere.

EXAMPLES

Example 1

Deoxydehydration in Dodecane

Comparison of Catalysts

The reaction was conducted by mixing 1.0 mmol of 1,2-tetradecanediol, 5 mol % of catalyst (calculated with respect to molybdenum), 2 ml of dodecane, and 50 mg of heptadecane (internal GC standard) in an open test tube and heating the reaction mixture to ~195° C. in a pre-heated aluminium heating block with stirring. After 60 min, the reaction was stopped and the mixture was diluted with acetone and analyzed by GC. A comparison of seven molybdenum catalysts is compiled in Table 1.

TABLE 1

Comparison of molybdenum catalysts for deoxydehydration of 1,2-tetradecanediol to 1-tetradecene.

| Entry | Catalyst[a] | Yield[b] (%) |
|---|---|---|
| 1 | $Mo(CO)_6$ | 40 |
| 2 | $Mo(CO)_4(bipy)$ | 43 |
| 3[c] | $MoO_2Cl_2(bipy)$ | 38 |
| 4[c] | $MoO_2Br_2(bipy)$ | 27 |
| 5 | $MoO_2(CH_3)_2(bipy)$ | 40 |
| 6 | $(NH_4)_6Mo_7O_{24} \cdot 4H_2O$ | 43 |

[a]bipy = 2,2'-bipyridine.
[b]Determined by GC using heptadecane as internal standard; the maximum theoretical yield is 50%.
[c]The catalyst was not completely soluble.

Comparison of Reductants

Four possible reductants, 3-octanol, $PPh_3$, 1-decanol, and benzyl alcohol, were compared by mixing 1.0 mmol of 1,2-tetradecanediol, 1.5 mmol of reductant, 5 mol % of $MoO_2(CH_3)_2(bipy)$, 2 ml of dodecane, and 50 mg of heptadecane (internal GC standard) in an open test tube and heating the reaction mixture to ~195° C. in a pre-heated aluminium heating block with stirring. After 60 min, the reaction was stopped and the mixture was diluted with acetone and analyzed by GC. The yields were 37% for 3-octanol, 57% for $PPh_3$, 29% for 1-decanol, and 8% for benzyl alcohol.

Variation of Reaction Conditions

The reaction conditions were varied by varying the temperature, catalyst concentration, and/or by adding acid or base. The reactions were conducted by mixing 1.0 mmol of 1,2-tetradecanediol, 1-5 mol % of $MoO_2(CH_3)_2(bipy)$, 2 ml of dodecane, 50 mg of heptadecane (internal GC standard), and possibly 3 mol % of acid or base in an open test tube and heating the reaction mixture to 180-205° C. in a pre-heated aluminium heating block with stirring. After 60 min (90 min for the experiment at 180° C.), the reaction was stopped and the mixture was diluted with acetone and analyzed by GC. The results are compiled in Table 2.

TABLE 2

Comparison of catalytic loading and temperature for the deoxydehydration of 1,2-tetradecanediol catalyzed by $MoO_2(CH_3)_2(bipy)$

| Entry | $X_{cat.}$ (%) | T (° C.) | Yield[a] (%) |
|---|---|---|---|
| 1 | 4.7 | 180 | 4 |
| 2 | 1.6 | 197 | 22 |
| 3 | 3.1 | 197 | 33 |
| 4 | 4.7 | 196 | 40 |
| 5 | 6.1 | 197 | 40 |
| 6 | 4.6 | 204 | 42 |
| 7[b] | 4.7 | 197 | 25 |
| 8[c] | 4.7 | 197 | 42 |
| 9[d] | 4.8 | 197 | 43 |

[a]Determined by GC using heptadecane as internal standard; the maximum theoretical yield is 50%.
[b]Addition of 5.9 mg (3.1 mol %) of TsOH•$H_2O$ - results in precipitation.
[c]Addition of 4.9 mg (3.4 mol %) of octanoic acid.
[d]Addition of 2.7 mg (2.5 mol %) of benzylamine.

Example 2

Deoxydehydration in the Neat Substrate

A mixture of 0.150 mol 17.7 g of 1,2-hexanediol was mixed with 0.5 mol % of catalyst (calculated with respect to molybdenum) and possibly 3 mol % of NaOH in a round-bottomed flask fitted with a distillation setup. The mixture was heated to 190-220° C. until no more volatile products distilled (16-18 h), and the distillate was analyzed by GC. The results are indicated in Table 3.

TABLE 3

Product distribution of Mo-catalyzed deoxydehydration conducted in neat 1,2-hexanediol

| Catalyst | Yield[a] of volatile products (%) | Yields[b] of 1-hexene/2-hexanone/1,2-epoxyhexane (%) |
|---|---|---|
| $MoO_2(CH_3)_2(bipy)$ | 62 | 13/5/— |
| $MoO_2Cl_2(bipy)$ | 63 | 19/6/— |
| $(NH_4)_6Mo_7O_{24} \cdot 4H_2O$ | 71 | 16/5/— |
| $(NH_4)_6Mo_7O_{24} \cdot 4H_2O$[c] | 65 | 13/6/22 |
| $Na_2MoO_4$ | 50 | 9/4/29 |

[a]Calculated as the mass of volatile products divided by the mass of 1,2-hexanediol.
[b]Determined by GC using toluene as internal standard; the maximum theoretical yield of 1-hexene is 50%.
[c]Addition of 190 mg (3.2 mol %) of NaOH.

Example 3

Deoxydehydration in 1,5-Pentanediol

A mixture of 0.030 mol of polyol (1,2-hexanediol or glycerol) was mixed with 2.5 mol % of $(NH_4)_6Mo_7O_{24} \cdot 4H_2O$ and 10 g of 1,5-pentanediol in a round-bottomed flask fitted with a distillation setup. The mixture was heated to 190-220° C. until no more volatile products distilled, and the distillate was analyzed by GC. The results are indicated in Table 4.

TABLE 4

Alkene yields (1-hexene and allyl alcohol) in 1,5-pentanediol and without solvent

| Polyol | 1,5-pentanediol | No solvent |
|---|---|---|
| 1,2-Hexanediol | 45% | 19% |
| Glycerol | 40% | 9% |

The invention claimed is:

1. A process for producing a reduced polyol comprising: reaction of the polyol with a substrate in the presence of a molybdenum catalyst at a temperature of at least 175° C., wherein the substrate is the polyol itself, a polyol different from the polyol being reduced, $H_2$, or a diol different from the polyol, wherein said molybdenum catalyst has the formula:

$$A^{\alpha+}{}_a(Mo_vX_xR^1_yR^2_zR^3_e)^{\alpha^* a-},$$

and wherein $A^{\alpha+}$ is a mono-, di-, or trivalent counterion;
X is CO, O, OH, S, or Se;
$R^1$ is selected from the group consisting of H, F, Cl, Br, I, CN, $N_3$, NCS, dithiocarbamates, $CH_3$, $BF_4$, $PF_6$, $SbF_6$, and $AsF_6$;
$R^2$ is a mono-, bi- or tridentate ligand;
$R^3$ is a ligand coordinating to the central molybdenum atom through its π-system selected from the group consisting of an alkene, a diene, a cyclopentadienyl, methylcyclopentadienyl, a pentamethylcyclopentadienyl radical, benzene, naphthalene, anthracene, and an aromatic;
a is 0, 1, 2, 3, 4, 5, or 6;
v is 1, 2, 3, 4, 5, 6, or 7;
x is in the range 2v to 6v;
y is 0, 1, 2, 3, 4, 5, 6, 7, or 8;
z is 0, 1, 2, or 3;
e is 0, 1, 2, or 3; and
α*a− is a negative charge, which balances the positive charge of $A^{\alpha+}a$, and wherein the process is carried out with a solvent, said polyol, said substrate, and said molybdenum catalyst being fully dissolved in said solvent;

and wherein the polyol is an alcohol containing a plurality of hydroxyl groups, wherein at least two of the hydroxyl groups are located on adjacent carbon atoms.

2. The process according to claim 1, wherein the temperature is in the range 175 to 250° C.

3. The process according to claim 1, wherein the polyol is a diol or a triol.

4. The process according to claim 3, wherein the polyol is selected from the group consisting of 1,2-hexanediol, 1,2-tetradecanediol, and glycerol.

5. The process according to claim 4, wherein the polyol is glycerol.

6. The process according to claim 1, wherein the substrate is the polyol itself, $H_2$, or a diol different from the polyol.

7. The process according to claim 6, wherein the substrate is a diol different from the polyol.

8. The process according to claim 1, wherein the amount of molybdenum catalyst is in the range 0.1 to 20 mol %.

9. The process according to claim 1, wherein $A^{\alpha+}$ is $Na^+$ or $NH_4^+$.

10. The process according to claim 1, wherein $R^2$ has one or more donor atoms selected from the group consisting of N, P, and S.

11. The process according to claim 10, wherein $R^2$ is 2,2'-bipyridine.

12. The process according to claim 1, wherein v is 1 or 7.

13. The process according to claim 1, wherein a is 0, 2, or 6.

14. The process according to claim 1, wherein the molybdenum catalyst is selected from the group consisting of $Mo(CO)_6$, $Mo(CO)_4(bipy)$, $MoO_2Cl_2(bipy)$, $MoO_2Br_2(bipy)$, $MoO_2(CH_3)_2(bipy)$, $(NH_4)_6Mo_7O_{24} \cdot 4H_2O$, $Na_2MoO_4$, and mixtures thereof, wherein bipy is 2,2'-bipyridine.

15. The process according to claim 1, wherein the resulting product having the highest molar percentage is the corresponding compound wherein at least one α,β-dihydroxyl group has been converted into an α,β-carbon-carbon double bond.

16. The process according to claim 2, wherein the temperature is in the range 180 to 220° C.

17. The process according to claim 2, wherein the temperature is in the range 190 to 210° C.

18. The process according to claim 2, wherein the temperature is in the range 195 to 205° C.

19. The process according to claim 8, wherein the amount of molybdenum catalyst is in the range 1 to 15 mol %.

20. The process according to claim 8, wherein the amount of molybdenum catalyst is in the range 2 to 10 mol %.

21. The process according to claim 8, wherein the amount of molybdenum catalyst is in the range 3 to 8 mol %.

22. The process according to claim 8, wherein the amount of molybdenum catalyst is in the range 4 to 7 mol %.

* * * * *